United States Patent [19]
Williams

[11] Patent Number: 5,318,030
[45] Date of Patent: Jun. 7, 1994

[54] AN APPLANATION TONOMETER DISINFECTING SYSTEM

[76] Inventor: Robert D. Williams, 4011 Talbot Rd. S. #210, Renton, Wash. 98055

[21] Appl. No.: 24,941
[22] Filed: Mar. 2, 1993
[51] Int. Cl.$^5$ .............................................. A61B 3/16
[52] U.S. Cl. ..................................... 128/652; 422/28; 422/292; 422/300
[58] Field of Search ............... 128/652, 645, 646, 647, 128/648, 649, 650, 651; 15/244.1, 250.1, 104.92, 104.93; 422/28, 292, 300; 118/264, 265, 270

[56] References Cited

U.S. PATENT DOCUMENTS

| | | | |
|---|---|---|---|
| 4,419,781 | 12/1983 | Meegan | 15/244.1 |
| 4,735,209 | 4/1988 | Foody | 128/652 |
| 5,053,207 | 10/1991 | Lervick | 422/28 |
| 5,185,900 | 2/1993 | Warner et al. | 15/104.92 |

Primary Examiner—Richard J. Apley
Assistant Examiner—John Mulcahy
Attorney, Agent, or Firm—Teresa J. Wiant

[57] ABSTRACT

A disinfecting system (10) for an applanating surface (12) of an applanation tonometer (16) includes an absorbent, deformable wick (18), a vial (40), and a holder (20). In use, the wick (18) is saturated with a disinfecting solution, then the applanating surface (12) of the tonometer (16) is brought into contact with the saturated wick (18) for approximately 10 to 15 minutes.

11 Claims, 2 Drawing Sheets

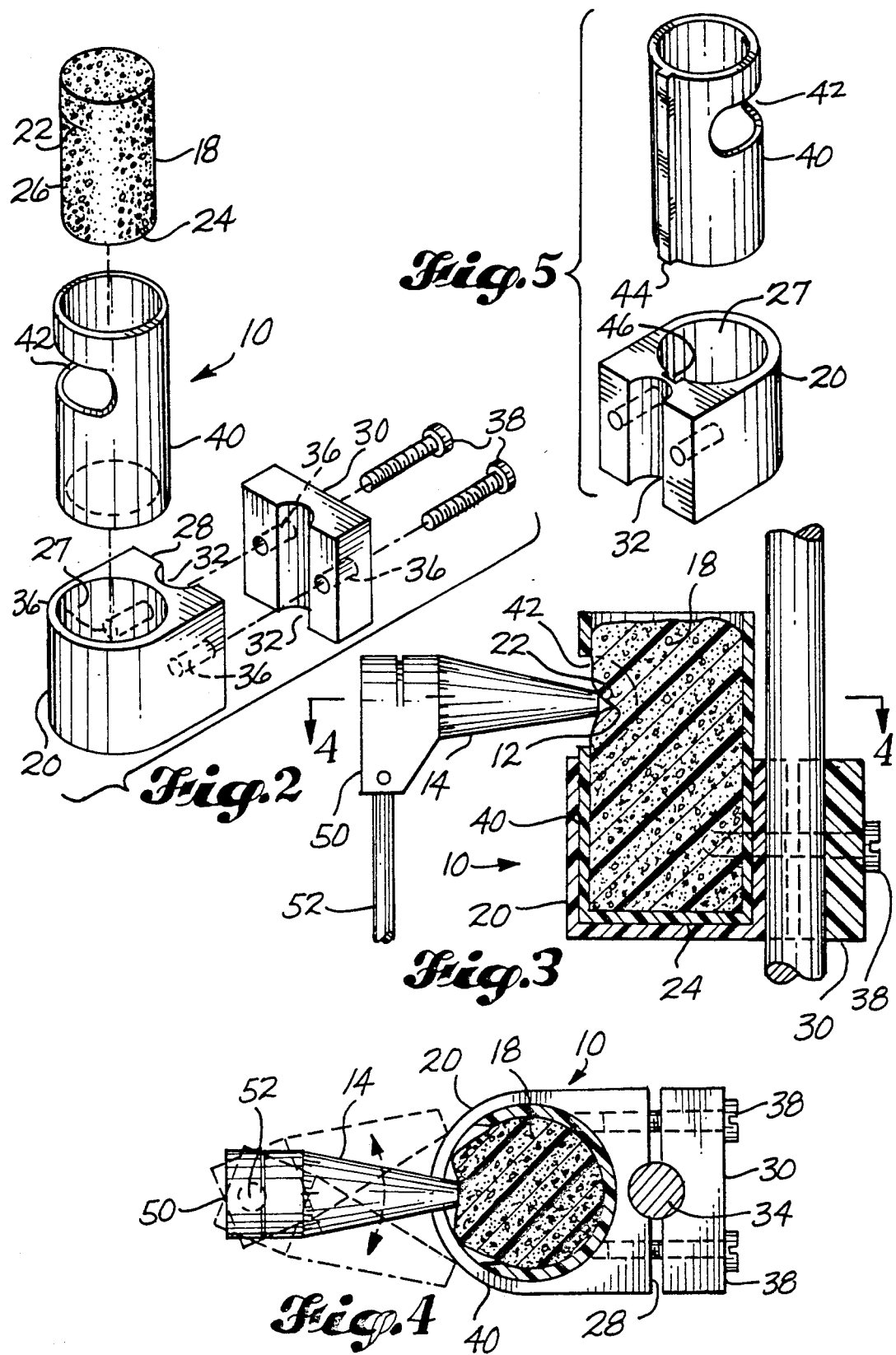

AN APPLANATION TONOMETER DISINFECTING SYSTEM

TECHNICAL FIELD

This invention relates to a disinfecting system for a corneal applanating surface of a tonometer, and more particularly, to such a disinfecting system comprising a porous wick, saturated with a disinfecting solution, with the wick held in a holder which is mounted on a slit lamp mounted applanation tonometer, and a method for disinfecting an applanating surface of a slit lamp mounted applanation tonometer.

BACKGROUND INFORMATION

The ocular pressure of an eye may be measured by a procedure using an applanation tonometer. A commonly used applanation tonometer is described in U.S. Pat. No. 3,070,997. According to the procedure, a planar applanating surface on a prism of the applanation tonometer is brought into contact with a cornea of an eye. The tonometer is adjusted until the surface of the cornea conforms substantially with the planar applanating surface and then a measurement is taken. Due to the applanating surface contacting the eye, the applanating surface is exposed to lacrimal fluid from the eye. The contamination of the applanating surface with the lacrimal fluid has been recognized as posing a risk of transmission of disease. Thus, the applanating surface should be disinfected between each use to prevent transmitting lacrimal fluid from one eye to another.

Prior methods for disinfecting the applanating surface require modification of the tonometer for installation of a disinfecting system or dismantling of the prism from the tonometer between each use.

SUMMARY OF THE INVENTION

The present invention provides a disinfecting system for a corneal applanating surface on a prism of a tonometer. The tonometer prism is rotatable about a vertical axis. The system comprises a porous wick and a holder. The wick is deformable for contacting and surrounding the applanating surface of the tonometer. The wick is saturated by a disinfecting solution. The disinfecting solution is capable of substantially disinfecting an applanating surface when the surface is in contact with the solution. The wick is mountable on the holder. The holder positions the wick such that when the tonometer prism is rotated about its vertical axis, the applanating surface of the tonometer prism is brought into contact with the wick. In preferred form, the wick comprises a slit. The slit is positioned for receiving the applanating surface.

Also in preferred form, when the wick is positioned such that it is deformed by the contact of the applanating surface with the wick, the wick is recoverable from being deformed. When the applanating surface is brought into contact with the wick multiple times for disinfecting the applanating surface multiple times, each time the wick deforms such that the applanating surface is substantially surrounded by the wick without the wick being deformed away from contact with the applanating surface.

In one form of the invention, the holder includes a vial. The vial receives the wick. The vial includes an opening for receiving the applanating surface through the opening, into the vial, and into the wick.

In preferred form, the tonometer is mounted on an arm. The arm is attached to a slit lamp. The holder is attached to the arm.

The present invention provides a method for disinfecting a corneal applanating surface on a prism of a tonometer. The tonometer prism is rotatable about a vertical axis. The method comprises providing a wick. The wick is saturated with a disinfecting solution. The wick is positioned such that it is within a path traveled by the tonometer prism as the tonometer prism is rotated about its vertical axis. The tonometer prism is operated such that the applanating surface is brought into contact with the surface of an eye. The tonometer is rotated about its vertical axis such that the applanating surface is brought into contact with the wick. Then, the applanating surface is allowed to be in contact with the wick for a time sufficient to disinfect the applanating surface. In a preferred form of the invention, the applanating surface is in contact with the saturated wick for at least approximately ten minutes.

These and other advantages and features will become apparent from the detailed description of the best mode for carrying out the invention that follows.

BRIEF DESCRIPTION OF THE DRAWINGS

In the drawings, like element designations refer to like parts throughout the several views, and:

FIG. 2 is an exploded view of the disinfecting system of the present invention;

FIG. 3 is a sectional plan view of an applanating surface on a prism of the slit lamp mounted applanation tonometer contacting a porous wick of the disinfecting system of the present invention;

FIG. 4 is a top sectional view taken across line 4—4 in FIG. 3 and showing the rotation of the prism of the applanation tonometer about a vertical axis; and FIG. 5 is another embodiment of a holder and a vial for use in the present invention.

BEST MODES FOR CARRYING OUT THE INVENTION

Figure 1:
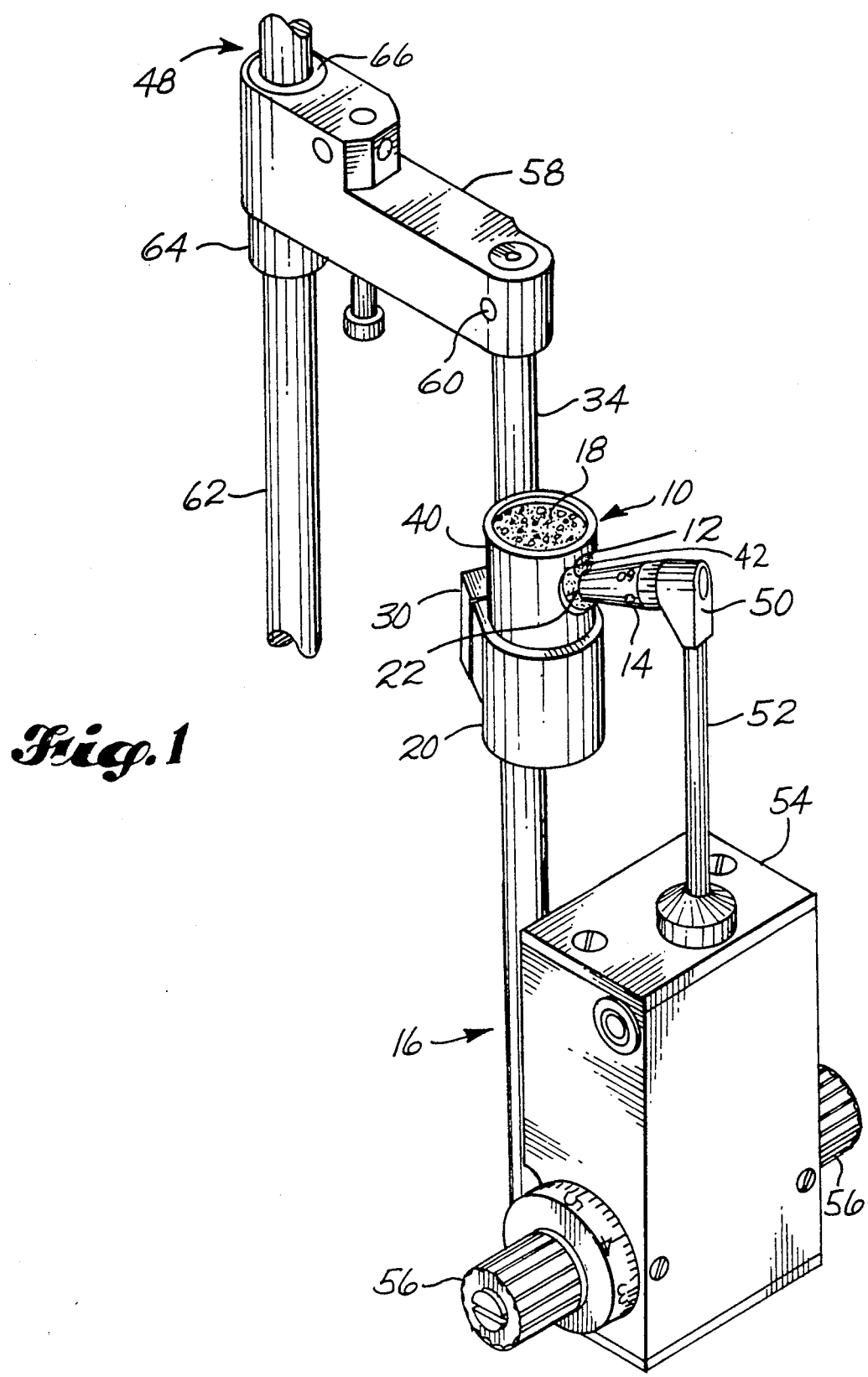
FIG. 1 is a pictorial view of a disinfecting system of the present invention mounted on a slit lamp mounted applanation tonometer.

The present invention provides a disinfecting system 10 for sterilizing a corneal applanating surface 12 on a prism 14 of a tonometer 16. As illustrated in FIGS. 1-4, the disinfecting system 10 includes an absorbent, deformable wick 18. The wick 18 is held in a holder 20, such that the applanating surface 12 may be brought into contact with the wick 18. In use, the wick 18 is saturated with a sterilizing solution. The applanating surface 12 is sterilized by being in contact with the saturated wick 18.

The wick 18 is constructed from a material which is capable of absorbing and holding a disinfecting liquid. During use, the wick 18 holds some of the liquid in a portion of the wick which is positioned for contact with the applanating surface 12 of the tonometer 16. The wick 18 should be constructed from a material which is deformable, such that the wick 18 is deformed when an applanating surface 12 is in contact with the wick 18, such that the wick 18 surrounds the applanating surface 12. The wicking material should have sufficient memory for recovering from a deformed position after the applanating surface 12 has been removed from the wick 18. The deformability and memory of the wick 18 should be sufficient to allow the same wick 18 to be used a plurality of times for sterilizing an applanating surface 2. Each time the applanating surface 12 is sterilized, the wick 18 should deform such that the applanating surface 12 is surrounded by the wick 18 and the disinfecting solution in the wick 18 is contacting substantially all of the applanating surface 12. In addition, each time the applanating surface 12 is removed from the wick 18, the wick 18 should have sufficient memory to recover from the deformed position such that the next time the applanating surface 12 is brought into contact with the wick 18, deformed portions of the wick 18 are not deformed out of contact with the wick 18. The wick 18 may be constructed from natural or synthetic materials, such as cotton, sponge or synthetic foam, exhibiting the required properties for this invention. Preferably, the wick 18 is constructed from a polyvinyl formyl foam sold by Mentor O & O of Massachusetts.

The wick 18 is saturated with a disinfecting solution which is capable of substantially sterilizing the applanating surface 12 such that viruses and bacteria will not be spread from one eye to another. Preferred disinfecting solutions are ethyl alcohol, isopropyl alcohol, 0.5% sodium hypochlorite, or 3% hydrogen peroxide. The applanating surface 12 should be in contact with the saturated wick 18 for at least approximately 10 minutes. In preferred form, the applanating surface 12 is in contact with the saturated wick 18 for between 10 to 15 minutes. The wick 18 should be substantially impervious to the disinfecting solution. The wick 18 should be capable of absorbing and holding the disinfecting solution without suffering substantial chemical or physical degradation.

In a preferred form of the invention, the wick 18 is provided with a slit 22. As illustrated in FIGS. 1 and 3, the slit 2 is positioned to receive the applanating surface 12 of the tonometer 16. The slit 22 enables the applanating surface 12 to enter into a portion of the wick 18 such that the applanating surface 12 and an end of the prism 14 are in contact with and surrounded by the wick 18.

As illustrated in FIGS. 1–4, the wick 18 may be cylindrical in shape, with a base 24 of the cylinder being supported by a holder 20 and the applanating surface 12 of the tonometer 16 contacting the wick 18 along a curved portion 26 of the wick 18.

According to the present invention, the wick 18 rests in the holder 20, such that the wick 18 is positioned in the path of the applanating surface 12 on the prism 14 of the tonometer 16, as illustrated in FIG. 4. The direction of rotation of the prism 14 is indicated by the arrows in FIG. 4.

As illustrated in FIG. 2, the holder 20 includes a cavity 27 for receiving the Wick 18. The wick 18 is positionable in the cavity 27 such that the slit 22 of the wick 18 is aligned with the path of the applanating surface 12 on the prism 14.

As illustrated in FIG. 2, the holder 20 may include a connecting portion 28 which is configured for securing to a mounting portion 30. The connecting portion 28 and the mounting portion 30 include recesses 32 which approximate a curve of a cylindrical arm 34. The mounting portion 30 and the connecting portion 28 further include screw holes 36 for receiving screws 38. In use, the connecting portion 28 of the holder 20 and the mounting portion 30 are placed around the cylindrical arm 34, then screws 38 are inserted through the screw holes 36 in the mounting portion 30, past the arm 34, and through the screw holes 36 in connecting portion 28 of the holder 20. The screws 38 are tightened such the holder 20 is held securely on the cylindrical arm 34. Preferably, the recesses 32 on the connecting portion 28 and the mounting portion 30 are configured to contact the cylindrical arm 34 for between ⅛ inch to 5 inches.

As illustrated in FIGS. 1–5, the disinfecting system 10 may further include a vial 40. The wick 18 is received within the vial 40, and the vial 40 and the wick 18 are received within the cavity 27 in the holder 20. In preferred form, the wick 18 is held in the vial 40 with the wick 18 substantially filling the vial 40. The vial 40 aids in retarding evaporation of the disinfecting solution from the wick 18. Also, the vial 40 holds the wick 18 securely such that the wick 18 is not substantially displaced by an applanating surface 12 contacting the wick 18. Preferably, the vial 40 has an internal diameter of between ⅛ inch to 3 inches.

As illustrated in FIGS. 1–5, the vial 40 may include a window or opening 42 in its side. The wick 18 should fill the vial 40 such that at least a portion of the wick 18 is accessible through the window or opening 42. The window 42 should be aligned in the holder 20 such that the applanating surface 12 on the prism 14 of the tonometer 16 may enter through the window 42 and contact the wick 18. FIG. 5 illustrates a preferred way of ensuring the alignment of the window 42 in the holder 20 by providing a key 44 on the vial 40 and a keyway 46 in the cavity 27 of the holder 20. The vial 40 may by inserted into the holder 20, with the key on the vial 40 entering the keyway 46 in the holder 20. The key 44 and keyway 46 provide a locking mechanism for insuring the alignment of the opening or window 42 in the vial 40 with the path of the applanating surface 12 on the prism 14 of the tonometer 16. Other similar locking mechanisms may be provided for ensuring the alignment of the vial 40 in the holder 20.

According to one form of the invention, the vial 40 is fitted with a cap (not shown). The cap covers the top of the vial 40 and aids in retarding evaporation of the disinfecting solution from the wick 18. The cap may be snap-fit to the vial 40, or the vial 40 may include threaded portions for receiving a screw-on type cap.

The vial 40, holder 20, and cap should be constructed from materials impervious to degradation by a disinfecting solution. The vial 40, holder 20, and cap may be constructed of a nonreactive metallic or polymer. Preferably, the vial 40 and holder 20 are constructed from polyethylene, or the vial 40 is constructed of polyethylene and the holder 20 is constructed from a nonreactive metal.

The system 10 may be constructed such that the wick 18 remains within the vial 40 and is saturated with more disinfecting solution as the solution evaporates from the wick 18. Also, the system 10 may be constructed such that fresh saturated wicks 18 are periodically replaced in the vial 40. In addition, a disposable saturated wick 18 in a vial 40 may be periodically replaced in the holder such that the wick 18 and vial 40 remain sanitary. In preferred form, a fresh saturated wick 18 is replaced in the system 10 during approximately every 4 hours of use of the system 10.

The disinfecting system 10 of the present invention is preferably used with a slit lamp 48 (partially shown) mounted applanation tonometer 16. As illustrated in FIG. 1, the applanation tonometer 16 includes the planar applanating surface 12 on the end of the tubular body tonometer prism 14. The tonometer prism 14 is held by a tonometer prism holder 50. The tonometer prism holder 50 is attached to a tonometer prism moment arm 52. The tonometer prism 14 may be rotated horizontally about the vertical axis of the tonometer prism moment arm 52, as illustrated by the arrows in FIG. 4. The tonometer prism moment arm 52 is connected to a body 54 of the tonometer 16. Dials 56 extend from the tonometer body 54. The dials 56 may be manipulated for taking measurements with the tonometer 16.

Still referring to FIG. 1, the tonometer 16 may be mounted on the slit lamp 48 by connecting the tonometer body 54 to the arm 34 of the slit lamp 48. The arm 34 of the slit lamp 48 is attached to a member 58 of the slit lamp 48 by a pin connection 60. The member 58 is attached to a rod 62 of the slit lamp 48 by a connection 64 which includes a bushing 66. The bushing 66 allows the member 58, and thus the tonometer 16, to be rotated horizontally about the vertical axis of the rod 62.

Typically, the slit lamp 48 provides lighting during an examination of an eye using an applanation tonometer 16 and other instrumentation. When the tonometer 16 is used to measure the pressure of an eye, the tonometer 16 is swung into a position relative to the eye by rotating the tonometer 16 horizontally about the vertical axis of the rod 62 of the slit lamp 48. Then, the applanating surface 12 of the prism 14 is positioned near the eye by rotating the prism 14 about the axis of the tonometer prism moment arm 52. The applanating surface 12 is brought into contact with the cornea of the eye by manipulating the dials 56 until the cornea approximately conforms to the applanating surface 12. After a measurement has been taken, the tonometer 16 is swung out of contact with the eye by rotating the tonometer prism 14 and the tonometer 16. Further examination of the eye may be conducted using the slit lamp 48 as a light source.

When the applanating surface 12 of the tonometer 16 contacts the cornea of the eye, the applanating surface 12 is contaminated by lacrimal fluids, such as tears and mucous, which may contain bacteria and viruses capable of transmitting infection or disease. The present invention enables the applanating surface 12 to be sterilized between uses without requiring that the tonometer 16 be dismantled or modified. Accordingly, the disinfecting system 10 is mounted such that after the applanating surface 12 has contacted a cornea of an eye, the applanating surface 12 may be brought into contact with the wick 18 saturated with a sterilizing solution. Preferably, the disinfecting system 10 is mounted on the arm 34 of the slit lamp 48 such that the wick 18 is positioned in the path of the applanating surface 12 on the prism 14 when the prism 14 is rotated about the vertical axis of the tonometer prism moment arm 52.

According to a preferred use of the present invention, the tonometer 16 is swung into a position to measure the pressure of an eye. After the pressure has been measured, the applanating surface 12 is removed from the cornea of the eye, and the prism 14 is rotated about the axis of the tonometer prism moment arm 52 such that the applanating surface 12 is brought into contact with the saturated wick 18, as illustrated in FIGS. 1, 3, and 4. Then, the tonometer 16 is rotated out of a position near the eye by rotating the tonometer 16 about the vertical axis of the rod 62. The applanating surface 12 remains in contact with the saturated wick 18 while the tonometer 16 is rotated and after the tonometer 16 has come to rest in a position away from the eye and out of the path of the light from the slit lamp, such that the tonometer 16 and the disinfecting system 10 do not interfere with the functioning of the slit lamp 48. Then, the slit lamp 48 may be used for examining the eye with other instrumentation. When the tonometer 16 is to be used again for measuring the pressure of an eye, the tonometer 16 may be swung towards a position relative to the eye by rotating the tonometer 16 about the vertical axis of the rod 62 and rotating the tonometer prism 14 such that the applanating surface 12 is rotated away from the wick 18 and towards the eye. Excess disinfecting solution may be wiped from the applanating surface 12 before the applanating surface 12 is brought into contact with the cornea of the eye. The applanating surface 12 should be in contact with the saturated wick 18 for at least ten minutes, but preferably for 10 to 15 minutes, before again being in contact with a cornea of an eye, such that the applanating surface 12 is substantially disinfected by the saturated wick 18.

The present invention provides a disinfecting system 10 which may be easily adapted for fitting a slit lamp mounted applanation tonometer 16 without removing the prism 14 from the tonometer 16 or altering the tonometer prism moment arm 52. The disinfecting system 10 is adaptable for use with various disinfecting solutions.

Although the preferred embodiments of the invention have been illustrated and described herein, it is intended to be understood by those skilled in the art that various modifications and omissions in form and detail may be made without departing from the spirit and scope of the invention as defined by the following claims.

What is claimed is:

1. A disinfecting system comprising:
    an applanation tonometer, said tonometer having a prism, said prism having a corneal applanating surface, said prism being rotatable about a vertical axis;
    a porous wick, said wick being deformable for contacting and surrounding said applanating surface, said wick being saturated by a disinfecting solution, said solution being capable of substantially disinfecting said applanating surface when said surface is in contact with said solution;
    a holder, said wick being mountable on said holder, said holder positioning said wick such that when said prism is rotated about said vertical axis, said applanating surface is brought into contact with said wick.

2. The disinfecting system of claim 1, wherein said wick is positioned such that it is deformed by the contact of said applanating surface with said wick, and said wick is recoverable from being deformed such that when said applanating surface is brought into contact with said wick multiple times for disinfecting said applanating surface multiple times, each time said wick deforms such that said applanating surface is substantially surrounded by said wick without said wick being deformed away from contact with said applanating surface.

3. The disinfecting system of claim 1, wherein said wick includes a slit, said wick being positioned such that said applanating surface is received in said slit.

4. The disinfecting system of claim 1, wherein said holder means includes a vial, said vial receiving said wick, and said vial including an opening for receiving said applanating surface through said opening, into said vial, and into said wick.

5. The disinfecting system of claim 4, wherein said wick includes a slit, said wick being positioned such that said applanating surface is received in said slit.

6. The disinfecting system of claim 1, further including a slit lamp having an arm wherein said holder is attached to said arm, and said tonometer is mounted on said arm.

7. A method for disinfecting a corneal applanating surface on a prism of a tonometer, said tonometer prism being rotatable about a vertical axis, comprising:
   providing a porous wick;
   saturating said wick with a disinfecting solution;
   positioning said wick such that said wick is in a path traveled by said tonometer prism as the tonometer prism is rotated about its vertical axis;
   operating said tonometer such that the applanating surface is brought into contact with a surface on an eye;
   rotating said tonometer prism about its vertical axis such that said applanating surface is brought into contact with said wick; and
   then, allowing said applanating surface to contact said wick for a time sufficient to disinfect said applanating surface.

8. The method of claim 7, wherein said applanating surface is in contact with said saturated wick for at least approximately 10 minutes.

9. A disinfecting system for a corneal applanating surface of a prism of a tonometer, comprising:
   a wick being deformable for contacting and surrounding an applanating surface of a tonometer, said wick being saturated by a disinfecting solution;
   a holder; and
   a vial, said vial being received in said holder, said wick being received in said vial, said vial including an opening in its side for receiving an applanating surface of a prism of a tonometer through said opening and into said wick;
   wherein in use, the tonometer is positioned relative to said disinfecting system with the prism of the tonometer being received through said opening in said vial and into said wick such that the prism of the tonometer is disinfected by said wick saturated with a disinfecting solution.

10. The disinfecting system of claim 9, wherein said wick further includes a slit, said slit being positioned for receiving the applanating surface of the tonometer.

11. The disinfecting system of claim 9, wherein said holder includes a keyway and said vial includes a key, said key and said keyway providing a locking mechanism for aligning said vial in said holder.

* * * * *

UNITED STATES PATENT AND TRADEMARK OFFICE
CERTIFICATE OF CORRECTION

PATENT NO. : 5,318,030
DATED : June 7, 1994
INVENTOR(S) : Robert D. Williams

It is certified that error appears in the above-identified patent and that said Letters Patent is hereby corrected as shown below:

Column 3, line 2, "surface 2" should be -- surface 12 --.

Column 3, line 36, "slit 2" should be -- slit 22 --.

Column 3, line 53, "Wick", first occurrence, should be -- wick --.

Claim 4, column 6, line 65, delete "means".

Signed and Sealed this

Eighteenth Day of October, 1994

Attest:

BRUCE LEHMAN

Attesting Officer    Commissioner of Patents and Trademarks